United States Patent
Demarais et al.

(10) Patent No.: US 7,756,583 B2
(45) Date of Patent: Jul. 13, 2010

(54) METHODS AND APPARATUS FOR INTRAVASCULARLY-INDUCED NEUROMODULATION

(75) Inventors: Denise Demarais, Los Gatos, CA (US); Nicolas Zadno, Fremont, CA (US); Benjamin J. Clark, Redwood City, CA (US); Erik Thai, San Jose, CA (US)

(73) Assignee: Ardian, Inc., Palo Alto, CA (US)

( * ) Notice: Subject to any disclaimer, the term of this patent is extended or adjusted under 35 U.S.C. 154(b) by 1139 days.

(21) Appl. No.: 11/266,993

(22) Filed: Nov. 4, 2005

(65) Prior Publication Data

US 2006/0142801 A1 Jun. 29, 2006

Related U.S. Application Data

(63) Continuation-in-part of application No. 11/129,765, filed on May 13, 2005, now Pat. No. 7,653,438, and a continuation-in-part of application No. 10/408,665, filed on Apr. 8, 2003, now Pat. No. 7,162,303, and a continuation-in-part of application No. 11/189,563, filed on Jul. 25, 2005.

(60) Provisional application No. 60/616,254, filed on Oct. 5, 2004, provisional application No. 60/624,793, filed on Nov. 2, 2004, provisional application No. 60/442,970, filed on Jan. 29, 2003, provisional application No. 60/415,575, filed on Oct. 3, 2002, provisional application No. 60/370,190, filed on Apr. 8, 2002.

(51) Int. Cl.
*A61N 1/00* (2006.01)
*A61N 1/30* (2006.01)

(52) U.S. Cl. .............................. 607/44; 607/116; 604/21

(58) Field of Classification Search ................ 607/2, 607/44, 116; 604/21
See application file for complete search history.

(56) References Cited

U.S. PATENT DOCUMENTS 3,650,277 A 3/1972 Sjostrand et al.
(Continued)

FOREIGN PATENT DOCUMENTS

DE 3151180 A1 8/1982
(Continued)

OTHER PUBLICATIONS

U.S. Appl. No. 11/504,117, Demarais et al.
(Continued)

*Primary Examiner*—Mark W Bockelman
(74) *Attorney, Agent, or Firm*—Perkins Coie LLP

(57) ABSTRACT

Methods and apparatus are provided for intravascularly-induced neuromodulation using a pulsed electric field, e.g., to effectuate irreversible electroporation or electrofusion, necrosis and/or inducement of apoptosis, alteration of gene expression, changes in cytokine upregulation, etc., in target neural fibers. In some embodiments, the intravascular PEF system comprises a catheter having a pair of bipolar electrodes for delivering the PEF, with a first electrode positioned on a first side of an impedance-altering element and a second electrode positioned on an opposing side of the impedance-altering element. A length of the electrodes, as well as a separation distance between the first and second electrodes, may be specified such that, with the impedance-altering element deployed in a manner that locally increases impedance within a patient's vessel, e.g., with the impedance-altering element deployed into contact with the vessel wall at a treatment site within the patient's vasculature, a magnitude of applied voltage delivered across the bipolar electrodes necessary to achieve desired neuromodulation is reduced relative to an intravascular PEF system having similarly spaced electrodes but no (or an undeployed) impedance-altering element. In a preferred embodiment, the impedance-altering element comprises an inflatable balloon configured to locally increase impedance within a patient's vasculature. The methods and apparatus of the present invention may be used to modulate a neural fiber that contributes to renal function.

19 Claims, 6 Drawing Sheets

U.S. PATENT DOCUMENTS

| | | | |
|---|---|---|---|
| 3,774,620 | A | 11/1973 | Hansjurgens |
| 3,895,639 | A | 7/1975 | Rodler |
| 5,006,119 | A | 4/1991 | Acker et al. |
| 5,019,034 | A * | 5/1991 | Weaver et al. ............... 604/20 |
| 5,094,242 | A | 3/1992 | Gleason et al. |
| 5,125,928 | A | 6/1992 | Parins et al. |
| 5,193,539 | A | 3/1993 | Schulman et al. |
| 5,193,540 | A | 3/1993 | Schulman et al. |
| 5,203,326 | A | 4/1993 | Collins et al. |
| 5,213,098 | A | 5/1993 | Bennett et al. |
| 5,282,785 | A | 2/1994 | Shapland et al. |
| 5,286,254 | A | 2/1994 | Shapland et al. |
| 5,304,120 | A | 4/1994 | Crandell et al. |
| 5,324,255 | A | 6/1994 | Passafaro et al. |
| 5,324,316 | A | 6/1994 | Schulman et al. |
| 5,334,193 | A | 8/1994 | Nardella |
| 5,338,662 | A | 8/1994 | Sadri |
| 5,405,367 | A | 4/1995 | Schulman et al. |
| 5,458,568 | A | 10/1995 | Racchini et al. |
| 5,458,626 | A | 10/1995 | Krause |
| 5,472,406 | A | 12/1995 | de la Torre et al. |
| 5,494,822 | A | 2/1996 | Sadri |
| 5,498,238 | A | 3/1996 | Shapland et al. |
| 5,499,971 | A | 3/1996 | Shapland et al. |
| 5,507,724 | A | 4/1996 | Hofmann et al. |
| 5,553,611 | A * | 9/1996 | Budd et al. ............... 600/374 |
| 5,569,198 | A | 10/1996 | Racchini |
| 5,571,147 | A | 11/1996 | Sluijter et al. |
| 5,626,576 | A | 5/1997 | Janssen |
| 5,628,730 | A | 5/1997 | Shapland et al. |
| 5,634,899 | A | 6/1997 | Shapland et al. |
| 5,690,691 | A | 11/1997 | Chen et al. |
| 5,725,563 | A | 3/1998 | Klotz |
| 5,792,187 | A | 8/1998 | Adams |
| 5,807,306 | A | 9/1998 | Shapland et al. |
| 5,861,021 | A | 1/1999 | Thome et al. |
| 5,865,787 | A * | 2/1999 | Shapland et al. ............... 604/21 |
| 5,871,449 | A | 2/1999 | Brown |
| 5,906,636 | A | 5/1999 | Casscells, III et al. |
| 5,916,154 | A | 6/1999 | Hobbs et al. |
| 5,919,187 | A | 7/1999 | Guglielmi et al. |
| 5,924,997 | A | 7/1999 | Campbell |
| 5,935,075 | A | 8/1999 | Casscells et al. |
| 6,026,326 | A | 2/2000 | Bardy |
| 6,051,017 | A | 4/2000 | Loeb et al. |
| 6,058,328 | A | 5/2000 | Levine et al. |
| 6,245,026 | B1 | 6/2001 | Campbell et al. |
| 6,251,130 | B1 | 6/2001 | Dobak, III et al. |
| 6,272,377 | B1 | 8/2001 | Sweeney et al. |
| 6,287,608 | B1 | 9/2001 | Levin et al. |
| 6,347,247 | B1 | 2/2002 | Dev et al. |
| 6,400,982 | B2 | 6/2002 | Sweeney et al. |
| 6,464,687 | B1 | 10/2002 | Ishikawa et al. |
| 6,482,619 | B1 | 11/2002 | Rubinsky et al. |
| 6,536,949 | B1 | 3/2003 | Heuser |
| 6,571,127 | B1 | 5/2003 | Ben-Haim et al. |
| 6,601,459 | B1 | 8/2003 | Jenni et al. |
| 6,613,045 | B1 * | 9/2003 | Laufer et al. ............... 606/27 |
| 6,615,071 | B1 | 9/2003 | Casscells, III et al. |
| 6,786,904 | B2 | 9/2004 | Doscher et al. |
| 6,927,049 | B2 | 8/2005 | Rubinsky et al. |
| 6,936,047 | B2 * | 8/2005 | Nasab et al. ............... 606/34 |
| 6,969,388 | B2 * | 11/2005 | Goldman et al. ............... 606/41 |
| 7,054,685 | B2 | 5/2006 | Dimmer et al. |
| 7,063,679 | B2 | 6/2006 | Maguire et al. |
| 7,081,114 | B2 | 7/2006 | Rashidi |
| 7,081,115 | B2 | 7/2006 | Taimisto |
| 7,083,614 | B2 | 8/2006 | Fjield et al. |
| 7,122,019 | B1 | 10/2006 | Kesten et al. |
| 2002/0026228 | A1 | 2/2002 | Schauerte |
| 2003/0055422 | A1* | 3/2003 | Lesh ............... 606/41 |
| 2003/0150464 | A1 | 8/2003 | Casscells |
| 2003/0199747 | A1 | 10/2003 | Michlitsch et al. |
| 2003/0199767 | A1 | 10/2003 | Cespedes et al. |
| 2003/0199768 | A1 | 10/2003 | Cespedes et al. |
| 2003/0236443 | A1 | 12/2003 | Cespedes et al. |
| 2004/0064090 | A1 | 4/2004 | Keren et al. |
| 2004/0064091 | A1 | 4/2004 | Keren et al. |
| 2004/0101523 | A1 | 5/2004 | Reitz et al. |
| 2004/0163655 | A1 | 8/2004 | Gelfand et al. |
| 2004/0167415 | A1 | 8/2004 | Gelfand et al. |
| 2004/0176699 | A1 | 9/2004 | Walker et al. |
| 2004/0249416 | A1 | 12/2004 | Yun et al. |
| 2005/0010263 | A1 | 1/2005 | Schauerte |
| 2005/0080459 | A1 | 4/2005 | Jacobson et al. |
| 2005/0153885 | A1 | 7/2005 | Yun et al. |
| 2005/0171523 | A1 | 8/2005 | Rubinsky et al. |
| 2005/0171574 | A1 | 8/2005 | Rubinsky et al. |
| 2005/0171575 | A1 | 8/2005 | Dev et al. |
| 2005/0209548 | A1 | 9/2005 | Dev et al. |
| 2005/0209642 | A1 | 9/2005 | Palti |
| 2005/0240241 | A1 | 10/2005 | Yun et al. |
| 2006/0041283 | A1 | 2/2006 | Gelfand et al. |
| 2006/0067972 | A1 | 3/2006 | Kesten et al. |
| 2006/0069323 | A1 | 3/2006 | Elkins et al. |
| 2006/0074453 | A1 | 4/2006 | Kieval et al. |
| 2006/0079859 | A1 | 4/2006 | Elkins et al. |
| 2006/0085046 | A1 | 4/2006 | Rezai et al. |
| 2006/0089674 | A1 | 4/2006 | Walters et al. |
| 2006/0100667 | A1 | 5/2006 | Machado et al. |
| 2006/0111754 | A1 | 5/2006 | Rezai et al. |
| 2006/0116720 | A1 | 6/2006 | Knoblich |
| 2006/0121016 | A1 | 6/2006 | Lee |
| 2006/0135998 | A1 | 6/2006 | Libbus et al. |
| 2006/0136004 | A1 | 6/2006 | Cowan et al. |
| 2006/0155344 | A1 | 7/2006 | Rezai et al. |
| 2006/0189941 | A1 | 8/2006 | Seward et al. |
| 2006/0189960 | A1 | 8/2006 | Kesten et al. |
| 2006/0190044 | A1 | 8/2006 | Libbus et al. |
| 2006/0206149 | A1 | 9/2006 | Yun |
| 2006/0229677 | A1 | 10/2006 | Moffitt et al. |
| 2006/0235474 | A1 | 10/2006 | Demarais |
| 2006/0265015 | A1 | 11/2006 | Demarais et al. |

FOREIGN PATENT DOCUMENTS

| | | |
|---|---|---|
| EP | 0811395 A2 | 6/1997 |
| WO | WO-85/01213 | 3/1985 |
| WO | WO-91/04725 | 4/1991 |
| WO | WO-93/02740 | 2/1993 |
| WO | WO-93/07803 | 4/1993 |
| WO | WO-94/00188 | 1/1994 |
| WO | WO-95/33514 | 12/1995 |
| WO | WO-96/04957 | 2/1996 |
| WO | WO-96/11723 | 4/1996 |
| WO | WO-97/13550 | 4/1997 |
| WO | WO 97/49453 | 12/1997 |
| WO | WO-98/37926 | 9/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-02/09808 | 2/2002 |
| WO | WO-02/26314 | 4/2002 |
| WO | WO-02/053207 | 7/2002 |
| WO | WO-02/070039 A2 | 9/2002 |
| WO | WO-02/070047 | 9/2002 |
| WO | WO-02/085448 | 10/2002 |
| WO | WO-03/018108 | 3/2003 |
| WO | WO-03/028802 | 4/2003 |
| WO | WO-03/063692 | 8/2003 |

| | | |
|---|---|---|
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005014100 | 2/2005 |
| WO | WO-2005016165 | 2/2005 |
| WO | WO-2005/032646 | 4/2005 |
| WO | WO-2005/065284 | 7/2005 |
| WO | WO-2005/084389 A2 | 9/2005 |
| WO | WO-2005/097256 A2 | 10/2005 |
| WO | WO-2005/123183 | 12/2005 |
| WO | WO-2006/007048 A2 | 1/2006 |
| WO | WO-2006018528 A1 | 2/2006 |
| WO | WO-2006/031899 A2 | 3/2006 |

OTHER PUBLICATIONS

U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
"Market for infusion pumps grows with an aging population," NWL Jan. 1997, The BBI Newsletter, vol. 20, No. 2, Feb. 1, 1997, American Health Consultants Inc., 6 pages.
"PHCL 762 Pharmacology of the Autonomic Nervous System," Chapter 2 and 6.8 in Mosby, http://www.kumc.edu/research/medicine/pharmacology/CAI/phcl762.html, last accessed Aug. 24, 2004, 14 pages.
"Programmable Infusion System," Pumps and Pump Selection, Medtronic Pain Therapies, Medtronic, Inc. Sep. 5, 2001, 2 pages.
"Pulmonary Concepts in Critical Care Breath Sounds," http://rnbob.tripod.com/breath.htm, last accessed Aug. 23, 2004, 5 pages.
"Pulmonary Function Testing," http://jan.ucc.nau.edu/~daa/lecture/pft.htm, last accessed Aug. 23, 2004, 8 pages.
"Renal Parenchymal Disease," Ch. 26, 5th Edition Heart Disease, A Textbook of Cardiovascular Medicine vol. 2, Edited by Eugene Braunwald, WB Saunders Company, pp. 824-825.
"Sensorcaine-MPF Spinal Injection," informational document, AstraZeneca 2001, 2 pages.
"Summary," Critical Reviews in Biomedical Engineering, vol. 17, Issue 5, 1989, pp. 515-529.
"The Antihypertensive and Lipid-Lowering Treatment to Prevent Heart Attack Trial," ALLHAT Research Group, JAMA 2002, vol. 288, pp. 2981-2997.
Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.
Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.
MacArthur, Dr. Alison, "Spinal Anesthesia and Severe Gestational Hypertension," presentation at Mount Sinai Hospital, 25 pages.
Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.
Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.
Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.
Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.
McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.
McCullough, Peter A., M.D., Mph et al., "Acute Renal Failure after Coronary Intervention: Incidence, Risk Factors and Relationship to Mortality," Apr. 14, 1997, AM J Med. 1997, vol. 103, 1997 Excerpta Medica, Inc., pp. 368-375.
McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.
McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.
Medtronic Neurostimulation Systems, "Expanding the Array of Pain Control Solutions," informational pamphlet, 1999 Medtronic, Inc., 6 pages.
Medtronic, "Spinal Cord Stimulation," Patient Management Guidelines for Clinicians, Medtronic, Inc. 1999, 115 pages.
Medtronic, "SynchroMed Infusion System—Clinical Reference Guide for Pain Therapy," Medtronic, Inc. 1998, 198 pages.
Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.
Mihran, Richard T. et al., "Temporally-Specific Modification of Myelinated Axon Excitability in Vitro Following A Single Ultrasound Pulse," Sep. 25, 1989, Ultrasound in Med.& Biol. 1990, vol. 16, No. 3, pp. 297-309.
Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba.
Mitchell, G.A.G., "The Nerve Supply of the Kidneys," Aug. 20, 1949, Acta Anatomica, vol. 10, Fasc. 1/2, 1950, pp. 1-37.
Moss, Nicholas G., "Renal function and renal afferent and efferent nerve activity," Am J Physiol 1982, vol. 243, © 1982, the American Physiological Society, pp. F425-F433.
Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.
Naropin (ropivacaine HCl) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nelson, Lawrence D. and Jeffrey L. Osborn, "Neurogenic Control of Renal Function in Response to Graded Nonhypotensive Hemorrahage in Conscious Dogs," Sep. 13, 1992, Am. J. Physiol. 264, 1993, American Physiological Society 1993, pp. R661-R667.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Nozawa, Takashi et al., "Effects of Long Term Renal Sympathetic Denervation on Heart Failure After Myocardial Infarction in Rats," Sep. 22, 2001, Heart Vessels 2002, vol. 16, Springer-Verlag 2002, pp. 51-56.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Podhajsky, R. J., et al. "The Histologic Effects of Pulsed and Continuous Radiofrequency Lesions at 42° C. to Rat Dorsal Root Ganglion and Sciatic Nerve," Spine, vol. 30, No. 9, 2005, Lippincott Williams & Wilkins Inc., pp. 1008-1013.

Popovic, Jennifer .R. and Margaret J. Hall, "1999 National Hospital Discharge Survey," Advance Data, No. 319, CDC, pp. 1-17 & 20.

Practice Guidelines Writing Committee and ESH/ESC Hypertension Guidelines Committee, "Practice Guidelines For Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ravalia, A. et al., "Tachyphylaxis and epidural anesthesia," Edgware General Hospital, Correspondence, p. 529.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Rump, L.C., "The Role of Sympathetic Nervous Activity in Chronic Renal Failure," J Clinical Basic Cardiology 2001, vol. 4, pp. 179-182.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Scheiner, Avram, Ph.D., "The design, development and implementation of electrodes used for functional electrical stimulation," Thesis paper, Case Western Reserve University, May 1992, 220 pages.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Scremin, Oscar U., M.D., Ph.D. and Danel P. Holschneider, M.D., "31. & 32. An Implantable Bolus Infusion Pump for the Neurosciences," FRP, Apr. 2005, 3 pages.

Shu-Qing, Liu et al., "Old spinal cord injury treated by pulsed electric stimulation," General Hospital of Beijing Command, Beijing, 5 pages (full article in Chinese; abstract on last page).

Shupak, Naomi M., "Therapeutic Uses of Pulsed Magnetic-Field Exposure: A Review," Radio Science Bulletin Dec. 2003, No. 307, pp. 9-32.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "Radiofrequency Part 2: Thoracic and Cervical Region, Headache and Facial Pain," various pages from, FlivoPress SA, Meggen (LU), Switzerland, 13 pages.

Sluijter, M.D., Ph.D., "The Role of Radiofrequency in Failed Back Surgery Patients," Current Review of Pain 2000, vol. 4, © 2000 by Current Science Inc., pp. 49-53.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.

Van Antwerp, Bill and Poonam Gulati., "Protein Delivery from Mechanical Devices Challenges and Opportunities," Medtronic Presentation, 19 pages.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Vigilance, Deon W. et al., "A Novel Approach to Increase Total Urine Output in Acute Heart Failure: Unilateral Renal nerve Blockade," RNB Abstract AHA, 2 pages.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Chapter 1: Electroporation Theory, Concepts and Mechanisms," Methods in Molecular Biology, vol. 55, Plant Cell Electroporation and Electrofusion Protocols, Edited by J.A. Nickoloff, © Humana Press Inc., pp. 3-28.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wilson, D.H. et al., "The Effects of Pulsed Electromagnetic Energy on Peripheral Nerve Regeneration," Annals New York Academy of Sciences, pp. 575-585.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Richard D., M.D., Ph.D., "Pharmacology of the Peripheral Nervous System," E-425 MSB, 6 pages.

Ye, Shaohua et al., "Renal Injury Caused By Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Yong-Quan, Dong et al., "The therapeutic effect of pulsed electric field on experimental spinal cord injury," Beijing Army General Hospital of People's Liberation Army, Beijing, 5 pages (full article in Chinese; abstract on last page).

Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.

Zundert, Jan Van, M.D. Fipp and Alex Cahana, M.D. Daapm, "Pulsed Radiofrequency in Chronic Pain Management: Looking for the Best Use of Electrical Current," Pain Practice 2005, vol. 5, Issue 2, © 2005 World Institute of Pain, pp. 74-76.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Guimaraes, Sarfim. "Vascular Adrenoceptors: An Update" pp. 319-356.

Hammer, Leah W. "Differential Inhibition of Functional Dilation of Small Arterioles by Indomethacin and Glibenclamide." Hypertension. Feb. 2001 Part II. pp. 599-603.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Janda, J., "Impact of the electrical stimulation apparatus rebox on the course of ischemic renal damage in rats," British Library-"The world's knowledge" pp. 252-254 (translated and untranslated versions).

U.S. Appl. No. 60/236,420, Harrison et al.
U.S. Appl. No. 60/370,190.
U.S. Appl. No. 60/408,665.
U.S. Appl. No. 60/415,575.
U.S. Appl. No. 60/442,970.

"Atrial Fibrillation" Heart and Vascular Health on Yahoo! Health. 2 pages <URL: http://health.yahoo.com/topic/heart/overview/article/healthwise/hw160872;_ylt=AiBT43Ey74HQ 7ft3jAb4C.sPu7cF>.

"Heart Arrhythmia" Heart and Vascular Health on Yahoo! Health. 13 pages <URL: http://health.yahoo.com/topic/heart/overview/article/mayoclinic/21BBE2B0-128D-4AA2-A5CE215065586678;_ylt=Aqd9M5rNyHD0sbPOmHX-FhLcPu7cF>.

"Isovue: Data Sheet". Regional Health Limited. 8 pages. Mar. 11, 2003.

"Micro ETS Hyperhidrosis USA" Hyperhidrosis USA. 2 pages. <URL: http://www.hyperhidrosis-usa.com/Index.html>.

Amersham Health. "Hypague-Cysto" 6 pages. 2003.

Arentz, Thomas et al. "Incidence of pulmonary vein stenosis 2 years after radiofrequency catheter ablation of refractory atrial fibrillation." European Heart Journal. 2003. 24; pp. 963-969.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Burkhoff, Daniel. "Interventional Device-Based Therapy For CHF Will Redefine Current Treatment Paradigms". Columbia University. 2004. 32 slides.

Canbaz, Suat et al. "Electrophysiological evaluation of phrenic nerve injury during cardiac surgery—a prospective, controlled clinical study." BioMed Central. 5 pages. 2004.

Carson, Peter. "Device-based Treatment For Chronic Heart Failure: Electrical Modulation of Myocardial Contractility". Transcatheter Cardiovascular Therapeutics 2005. 21 slides.

Chiou, CW et al. "Efferent Vagal Innervation of the Canine Atria and Sinus and Atrioventricular Nodes". Circulation. Jun. 1997. 95(11):2573-2584. Abstract only. 2 pages.

Cryovascular Systems, Inc. "Pre-Clinical Testing Establishing Parameters". PowerPoint Presentation. 18 slides.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005. pp. 845-852.

Fava, M. "Clinical Testing Establishing Safety & Efficacy". PowerPoint Presentation. Cryovascular Systems, Inc. 14 slides.

Fava, M. et al. "Initial Human Experience with CryoPlasty™ in the Treatment of Infrainguinal Arterial Disease." Abstract. 1 page.

Fischell, Tim A. et al. "Ultrasonic Energy: Effects on Valcular Function and Integrity," Circulation: Journal of the American Heart Association. 1991. 84;pp. 1783-1795.

Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.

International Search Report, PCT/US04/38498, Mailed Feb. 18, 2005, Applicant: G & L Consulting, LLC (3 pages).

Jia, Jianping and Pollock, Martin. "The pathogenesis of non-freezing cold nerve injury: Observations in the rat." Brain. 120; pp. 631-646. 1997.

Jia, Jianping et al. "Cold injury to nerves is not due to ischaemia alone." Brain. 121;pp. 989-1001. 1998.

Jin, Yuanzhe. et al. "Pulmonary Vein Stenosis and Remodeling After Electrical Isolation for Treatment of Atrial Fibrillation: Short- and Medium-Term Follow-Up," PACE, vol. 27. pp. 1362-1370. Oct. 2004.

Joye, James D. and Tatsutani, Kristine. "In Vitro Studies of Arterial Freezing Injury". 4 pages.

Joye, James D. and Tatsutani, Kristine. "In Vivo Study of Endovascular Cryotherapy for the Prevention of Restenosis." 4 pages.

Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.

Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. pp. 250-254.

Lee, Michael A. (editor). SPORTSMed. Connecticut State Medical Society Committee on the Medical Aspects of Sports. Fall/Winter 2005. 10 pages.

Mathur, Vandana S. "Intra-Renal Drug Delivery for Fluid Overload". FlowMedica. Transcatheter Cardiovascular Therapeutics 2005. 31 slides.

Mehran, Roxana. "Renal insufficiency and contrast nephropathy: The most common, least understood risk factor". Cardiovascular Research Foundation. Columbia University Medical Center. 2005. 86 slides.

Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005. pp. 546-554.

Pappone, Carlo and Santinelli, Vincenzo. [2005][P2-70] Safety Report of Circumferential Pulmonary Vein Ablation. A 9-Year Single-Center Experience on 6,442 Patients with Atrial Fibrillation. Abstract only. 1 page.

Pappone, Carlo et al. "[2004][759] Pulmonary Vein Denervation Benefits Paroxysmal Atrial Fibrillation Patients after Circumferential Ablation." Abstract only. 1 page.

Purerfellner, Helmut and Martinek, Martin. "Pulmonary vein stenosis following catheter ablation of atrial fibrillation," Current Opinion in Cardiology, 20; pp. 484-490. 2005.

Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.

Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.

Sabbah, Hani N. "Animal Models for Heart Failure and Device Development". Henry Ford Health System. 24 slides.

Schauerte, P et al. "Catheter ablation of cardiac autonomic nerves for prevention of vagal atrial fibrillation." Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P. et al. "Transvenous parasympathetic nerve stimulation in the inferior vena cava and atrioventricular conduction." Journal of Cardiovascular Electrophysiology. 11(1). Jan. 2000. Abstract only. 2 pages.

Scherlag, BJ and Po, S. "The intrinsic cardiac nervous system and atrial fibrillation." Current Opinion in Cardiology. 21(1):51-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Serrador, Jorge M. "Autonomic Regulation of the Cardiovascular System". MIT Lecture. 8 pages, 48 slides.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Sobotka, Paul A. "Treatment Strategies for Fluid Overload, CHF Patients". CHF Solutions. Transcatheter Cardiovascular Therapeutics 2005. 20 slides.

Steffen, W. et al. "Catheter-delivered high intensity, low frequency ultrasound induces vasodilation in vivo." European Heart Journal. 1994. 15;pp. 369-376.

Steg, PG et al. "Pulsed ultraviolet laser irradiation produces endothelium-independent relaxation of vascular smooth muscle". Circulation: Journal of the American Heart Association. 1989. pp. 189-197.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. pp. 184-189.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.

Terashima, Mitsuyasu et al. "Feasibility and Safety of a Novel CryoPlasty™ System". Poster. 1 page.

Thomas, John R. and Oakley, E. Howard N. "Chapter 15: Nonfreezing Cold Injury" *Medical Aspects of Harsh Environments*, vol. 1. pp. 467-490.

Vince, D. Geoffrey. "Virtual Histology: A new technique for the assessment of plaque composition". The Cleveland Clinic Foundation. 28 pages.

Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.

\* cited by examiner

METHODS AND APPARATUS FOR INTRAVASCULARLY-INDUCED NEUROMODULATION

CROSS-REFERENCE TO RELATED APPLICATIONS

The present application is a continuation-in-part of U.S. patent application Ser. No. 11/129,765, filed on May 13, 2005, now U.S. Pat. No. 7,653,438 which claims the benefit of U.S. Provisional Application Nos. 60/616,254, filed on Oct. 5, 2004; and 60/624,793, filed on Nov. 2, 2004. Further, this application is a continuation-in-part of U.S. patent application Ser. No. 10/408,665, filed on Apr. 8, 2003 (published as United States Patent Publication 2003/0216792 on Nov. 20, 2003 now U.S. Pat. No. 7,162,303), which claims the benefit of U.S. Provisional Patent Application Nos. 60/442,970, filed on Jan. 29, 2003; 60/415,575, filed on Oct. 3, 2002; and 60/370,190, filed on Apr. 8, 2002. Further, the present application is a continuation-in-part of co-pending U.S. patent application Ser. No. 11/189,563, filed on Jul. 25, 2005.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. More particularly, the present invention relates to methods and apparatus for achieving neuromodulation via an intravascularly-delivered pulsed electric field.

BACKGROUND

Congestive Heart Failure ("CHF") is a condition that occurs when the heart becomes damaged and reduces blood flow to the organs of the body. If blood flow decreases sufficiently, kidney function becomes impaired, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to vasoconstriction of blood vessels supplying the kidneys, decreased renal blood flow, decreased removal of water and sodium from the body, and increased renin secretion. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, co-pending U.S. patent application Ser. No. 11/129,765, filed on May 13, 2005, and Ser. No. 11/189,563, filed on Jul. 25, 2005, now abandoned, both of which are incorporated herein by reference in their entireties. A pulsed electric field (PEF) may initiate renal neuromodulation, e.g., denervation, for example, via irreversible electroporation or via electrofusion. The PEF may be delivered from apparatus positioned intravascularly, extravascularly, transvascularly or a combination thereof. As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

In some patients, when a PEF sufficient to initiate irreversible electroporation is applied to renal nerves and/or other neural fibers that contribute to renal neural functions, applicants believe that denervation induced by the PEF would result in increased urine output, decreased plasma renin levels, decreased tissue (e.g., kidney) and/or urine catecholamines (e.g., norepinephrine), increased urinary sodium excretion, and/or controlled blood pressure. Such responses would prevent or treat CHF, hypertension, renal system diseases, and other renal or cardio-renal anomalies. PEF systems could be used to modulate efferent or afferent nerve signals, as well as combinations of efferent and afferent nerve signals.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005 now abandoned, incorporated by reference as set forth above. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

Even when monitoring techniques are utilized, the applied energy or voltage from an intravascular PEF system necessary to establish an electric field of sufficient magnitude to modulate target neural fibers that contribute to renal function may be of a magnitude that causes persistent damage to non-target tissue, such as smooth muscle cells of the vessel wall. Thus, a desired treatment outcome, e.g., renal denervation, may not be achievable with some intravascular PEF systems in certain patients without concomitantly inducing persistent damage to the non-target tissue. It therefore would be desirable to provide methods and apparatus for reducing the required magnitude of applied voltage delivered from an intravascular PEF system necessary to achieve desired neuromodulation in target tissue.

SUMMARY

The present invention provides methods and apparatus for achieving neuromodulation via an intravascularly-delivered pulsed electric field ("PEF"). In some embodiments, the intravascular PEF system comprises a catheter having a pair of bipolar electrodes for delivering the PEF, with a first electrode positioned on a first side of an impedance-altering element and a second electrode positioned on an opposing side of the impedance-altering element. A length of the electrodes as well as a separation distance between the first and second electrodes may be specified such that, with the impedance-altering element deployed in a manner that locally increases impedance within a patient's vessel, a magnitude of applied voltage delivered across the bipolar electrodes necessary to achieve desired neuromodulation is reduced relative to an intravascular PEF system having similarly spaced electrodes but no (or an undeployed) impedance-altering element. For example, the impedance-altering element can be deployed to contact the vessel wall at a treatment site within the patient's vasculature to locally increase the impedance within a vessel. In a preferred embodiment, the impedance-altering element comprises an inflatable balloon configured to locally increase impedance within a patient's vasculature. The methods and apparatus of the present invention may be used to modulate a neural fiber that contributes to renal function.

Pulsed electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. Suitable field strengths include, for example, strengths of up to about 10,000 V/cm. Suitable pulse widths include, for example, widths of up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, combinations thereof, etc. Suitable numbers of pulses include, for example, at least one pulse. Suitable pulse intervals include, for example, intervals less than about 10 seconds. These parameters are provided for the sake of illustration and should in no way be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

The present invention relates to methods and apparatus for neuromodulation, e.g., denervation. More particularly, the present invention relates to methods and apparatus for achieving neuromodulation via an intravascularly-delivered pulsed electric field. In some embodiments, the intravascular PEF system comprises a catheter having a pair of bipolar electrodes for delivering the PEF, with a first electrode positioned on a first side of an impedance-altering element and a second electrode positioned on an opposing side of the impedance-altering element. A length of the electrodes, as well as a separation distance between the first and second electrodes, may be specified such that a magnitude of applied voltage delivered across the bipolar electrodes necessary to achieve desired neuromodulation is reduced relative to an intravascular PEF system having similarly spaced electrodes but no (or an undeployed) impedance-altering element.

The methods and apparatus of the present invention may be used to modulate a neural fiber that contributes to renal function and may exploit any suitable electrical signal or field parameters, e.g., any electric field that will achieve the desired neuromodulation (e.g., electroporative effect). To better understand the structures of devices of the present invention and the methods of using such devices for renal neuromodulation and monitoring, it is instructive to examine the renal anatomy in humans.

B. Selected Embodiments of Methods for Neuromodulation

Figure 1:
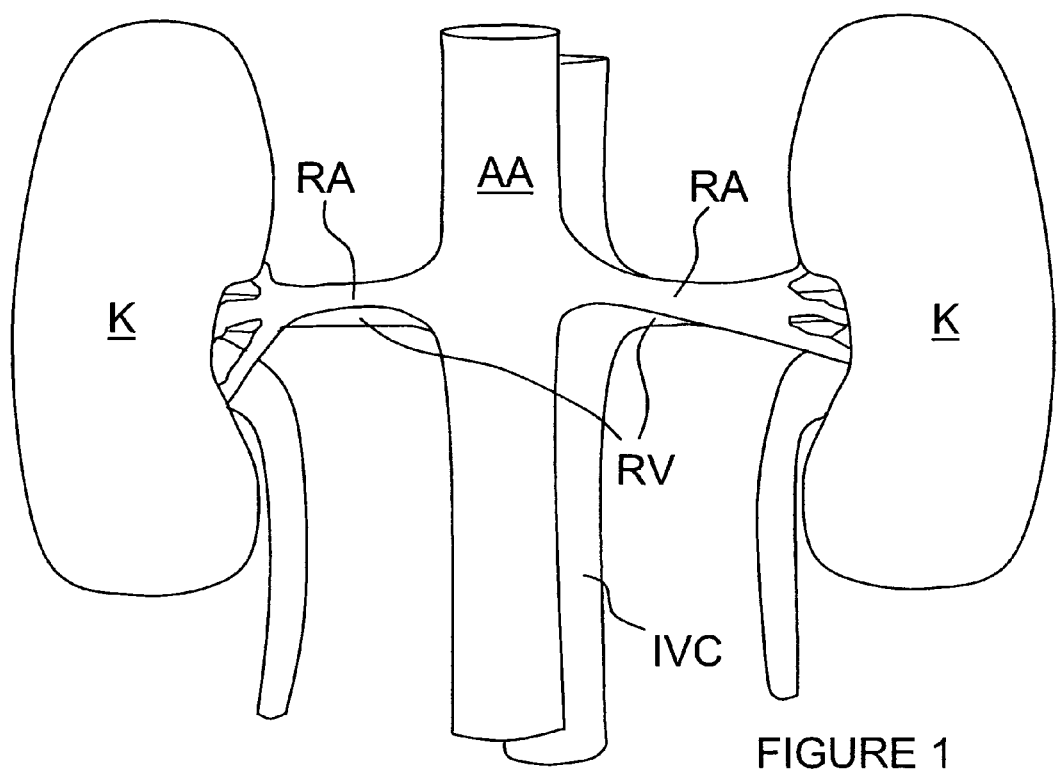
FIG. 1 is a schematic view illustrating human renal anatomy.
Figure 2:
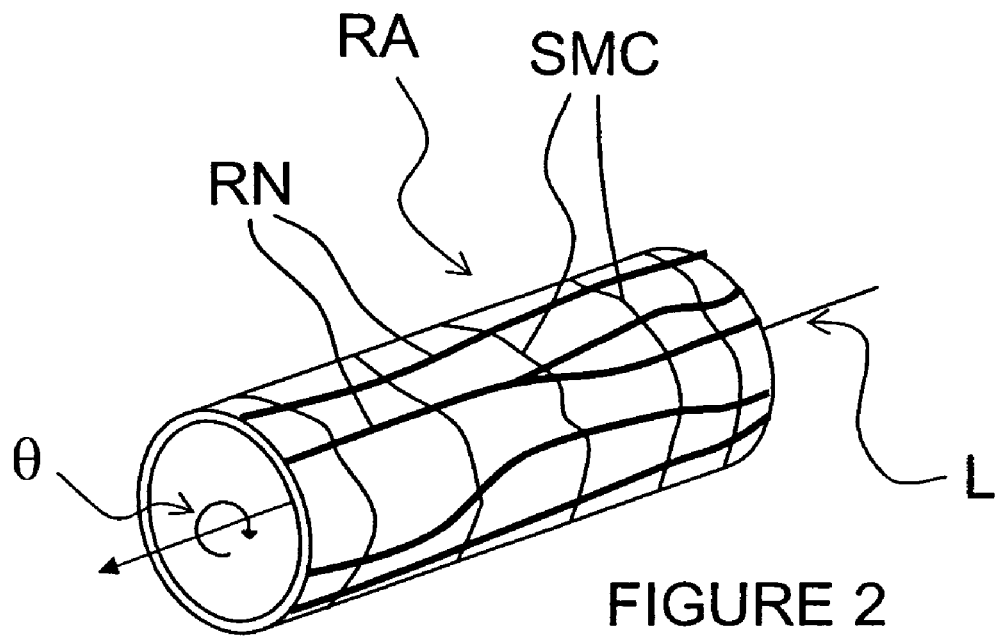
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
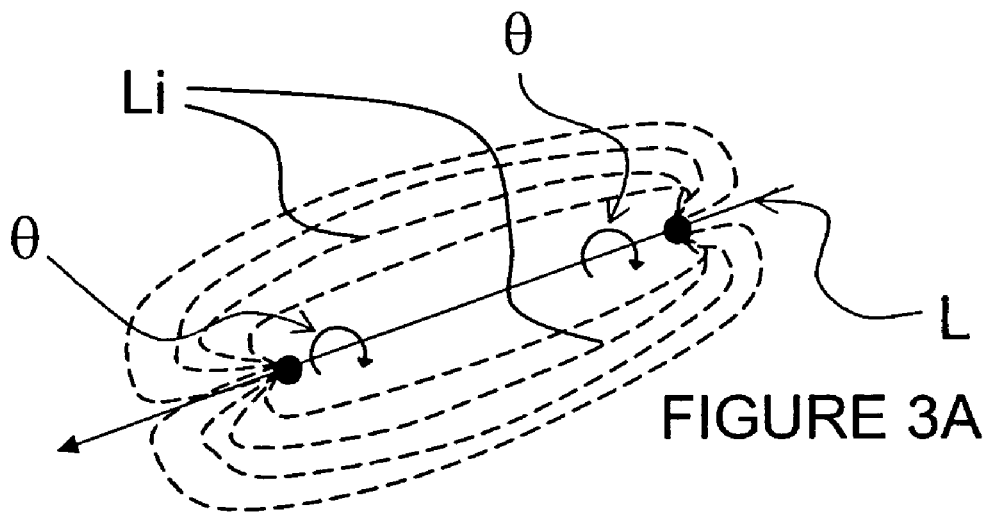
FIGS. 3A and 3B are schematic side- and end-views, respectively, illustrating orienting of an electric field for selectively affecting renal nerves.
Figure 3B:
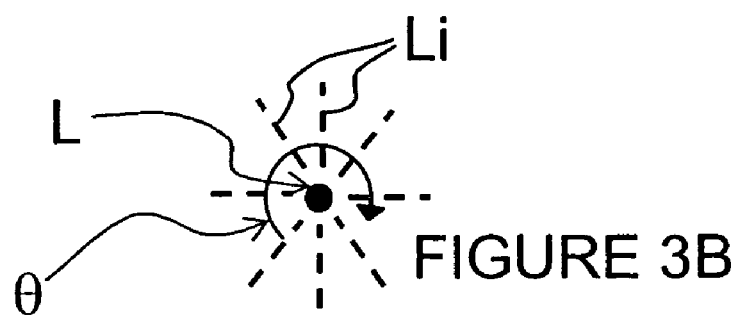

Referring to FIG. 3, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, several embodiments of electrodes of the present invention are configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to change cytokine upregulation, etc. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or at least partially across the wall of the renal artery may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

C. Exemplary Embodiments of Systems and Additional Methods for Neuromodulation With reference to FIG. 4, an embodiment of an intravascular PEF system and method is described. The system is configured for temporary intravascular placement. Furthermore, the system is configured to deliver a pulsed electric field to neural fibers for neuromodulation, e.g., to deliver the pulsed electric field to neural fibers that contribute to renal function in order to achieve renal neuromodulation. Intravascular pulsed electric field apparatus 100 comprises catheter 102 having a pair of bipolar electrodes 104 positioned along the shaft of the catheter. The electrodes are electrically connected to pulsed electric field generator 50 located external to the patient. The generator may be utilized with any embodiment of the present invention for delivery of a PEF with desired field parameters. It should be understood that PEF-delivery electrodes of embodiments described hereinafter may be electrically connected to the generator, even though the generator is not explicitly shown or described with each embodiment. The electrodes may, for example, be fabricated from wound coils of wire. When utilizing relatively long electrodes, wound coils allow the catheter to maintain a desired degree of flexibility.

In use, catheter 102 may, for example, be delivered to renal artery RA as shown, or may be delivered to a renal vein or to any other vessel in proximity to neural tissue contributing to renal function, for example, through a guide catheter. Once positioned within the patient's vasculature, a pulsed electric field may be generated by the PEF generator 50, transferred through catheter 102 to electrodes 104, and delivered via the electrodes 104 across the wall of the vasculature. The PEF therapy modulates the activity along neural fibers, for example, along neural fibers that contribute to renal function, e.g., denervates the neural fibers. This may be achieved, for example, via irreversible electroporation, electrofusion, necrosis and/or inducement of apoptosis in the nerve cells, alteration of gene expression, changes in cytokine upregulation, etc. In many applications, including that shown in FIG. 4, the electrodes are arranged so that the pulsed electric field is aligned with the longitudinal dimension of the renal artery to facilitate modulation of renal nerves with limited effect on non-target smooth muscle cells or other cells.

It is expected that PEF therapy will alleviate clinical symptoms of CHF, hypertension, renal disease and/or other cardio-renal diseases for a period of months, potentially up to six months or more. This time period might be sufficient to allow the body to heal; for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

In order to denervate target neural fibers, apparatus 100 must generate an electric field of sufficient strength or magnitude across the fibers to induce such denervation. Depending upon the arrangement and positioning of electrodes 104 and catheter 102, as well as the physiology of the patient, the applied voltage necessary to achieve a field strength of sufficient magnitude at the neural fibers might also be of sufficient magnitude to induce undesirable persistent injury in non-target tissue, such as smooth muscle cells and/or the vessel wall. It therefore would be desirable to provide apparatus and methods that reduce the necessary applied voltage for intravascular renal denervation via PEF therapy, as compared to the applied voltage required when utilizing apparatus 100.

Figure 5:
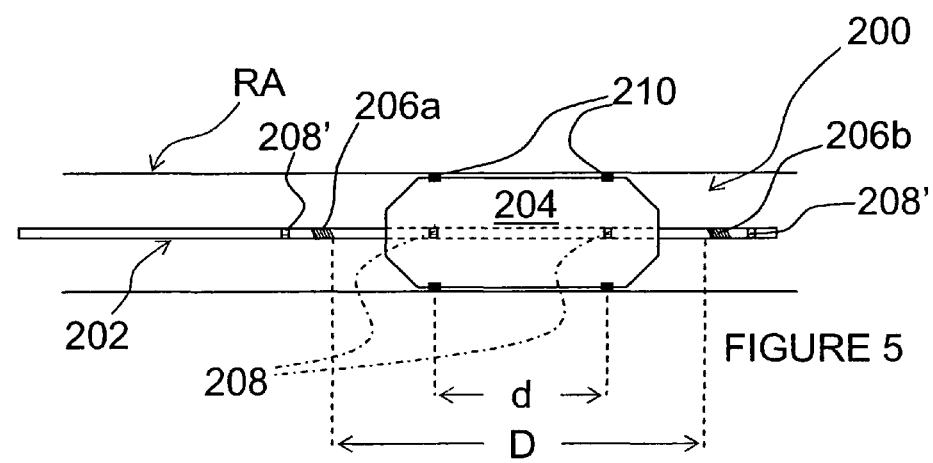
FIG. 5 is a schematic view illustrating an intravascular method and apparatus of the present invention.

Referring now to FIG. 5, an embodiment of an intravascular PEF system of the present invention is described. This embodiment includes an apparatus 200 comprising a catheter 202 having impedance-altering element 204, such as an inflatable balloon, an expandable cage (e.g., a polymer-coated expandable wire cage) or some other expandable element. Several embodiments of the impedance altering element 204 are configured to center electrodes 206 within a vessel. In a preferred embodiment, impedance-altering element 204 is configured to locally increase impedance within a patient's vasculature. In a further preferred embodiment, impedance-altering element 204 comprises an inflatable balloon, as shown in FIG. 5.

PEF-delivery electrodes 206a and 206b are positioned along the shaft of catheter 202 with known separation distance D; and optional radiopaque markers 208 are positioned along the shaft of the catheter in the region of impedance-altering element 204. The radiopaque markers 208 can be spaced apart from each other along a balloon-type impedance-altering element by known separation distance d. The electrodes 206a-b, for example, can be arranged such that the electrode 206a is near a proximal end of element 204 and the electrode 206b is near a distal end of the element 204. Electrodes 206 are electrically coupled to pulse generator 50 (see FIG. 4), which is positioned external to the patient, for delivery of PEF therapy. Radiopaque markers additionally or alternatively may be located along the shaft of catheter 202 outside of element 204, as illustrated by radiopaque markets 208'. As yet another alternative or addition, electrodes 206 may be fabricated from a radiopaque material, such as platinum, and utilized as radiopaque markers.

Apparatus 200 may further comprise optional monitoring electrodes 210, illustratively also with known separation distance d. Applicants have previously described the use of such monitoring electrodes to monitor tissue impedance or conductivity for determining the effects of pulsed electric field therapy, e.g., for determining an extent of electroporation and/or its degree of irreversibility. See, for example, Applicant's co-pending U.S. patent application Ser. No. 11/233, 814, filed Sep. 23, 2005 now abandoned, which is incorporated herein by reference as set forth above. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after termination of the pulsed electric field. Thus, monitoring of the impedance or conductivity of target and/or non-target tissue via electrodes 210 may be utilized to determine the onset of electroporation and/or to determine the type or extent of electroporation. Furthermore, monitoring data may be used in one or more manual or automatic feedback loops to control the electroporation.

Regardless of whether the effects of PEF therapy are monitored, the magnitude of voltage applied across electrodes 206 in order to establish an electric field of sufficient magnitude to modulate target neural fibers that contribute to renal function also might be of a magnitude that causes persistent damage to non-target tissue, such as smooth muscle cells of the vessel wall. Thus, a desired treatment outcome, e.g., renal denervation, might not be achievable in certain patients without concomitantly inducing persistent damage to the non-target tissue.

In accordance with the principles of the present invention, impedance-altering element 204 may reduce the magnitude of voltage applied across electrodes 206 that is required to modulate the target neural fibers. In some patients, this reduction in magnitude might lower the applied voltage below a threshold level that would cause the undesirable persistent damage to the non-target tissue. Element 204 may achieve this reduction in applied voltage magnitude, for example, by locally increasing impedance within the renal vasculature. Element 204 additionally or alternatively may facilitate use of a common applied voltage across a wider range of vessel sizes.

In embodiments where the impedance-altering element 204 comprises an inflatable balloon configured to temporarily occlude blood flow during delivery of PEF therapy across electrodes 206, the occluding balloon may serve as an electrical insulator that locally increases electrical impedance during PEF delivery. This impedance increase may direct an electric field delivered across electrodes 206, e.g., may direct the electric field into or across the vessel wall for modulation of target neural fibers. The impedance-altering element 204 electrically insulates a portion of the vessel in a manner that may reduce the magnitude of applied voltage or other parameters of the pulsed electric field necessary to achieve a desired field strength at the target fibers compared to apparatus 100 of FIG. 4 that does not comprise an impedance-altering element. The desired field strength, for example, may have a magnitude sufficient to denervate the target fibers via electroporation. As discussed, this reduction may moderate persistent damage to the non-target tissue. Furthermore, by substantially centering electrodes 206 within the vessel before delivery of PEF therapy, element 204 may further reduce a potential of persistent damage to the non-target tissue of the vessel wall, etc., and/or may facilitate delivery of a more concentrically uniform electric field to the target neural fibers surrounding the renal artery. In addition, or as an alternative, to the use of balloon element 204 to achieve a desired insulation or impedance increase within a patient's vasculature between electrodes 206 during delivery of PEF therapy, the impedance change may be achieved via an insulative covering, e.g., via a polymeric tube or sleeve with closed ends, positioned about a mechanical activation member. The mechanical activation member may be configured to expand the insulative covering into, e.g., circumferential sealing contact with the vessel wall. The mechanical activation member may, for example, comprise an expandable cage. Additional methods and apparatus in accordance with the present invention for achieving the desired impedance change will be apparent to those of skill in the art.

Figure 6:
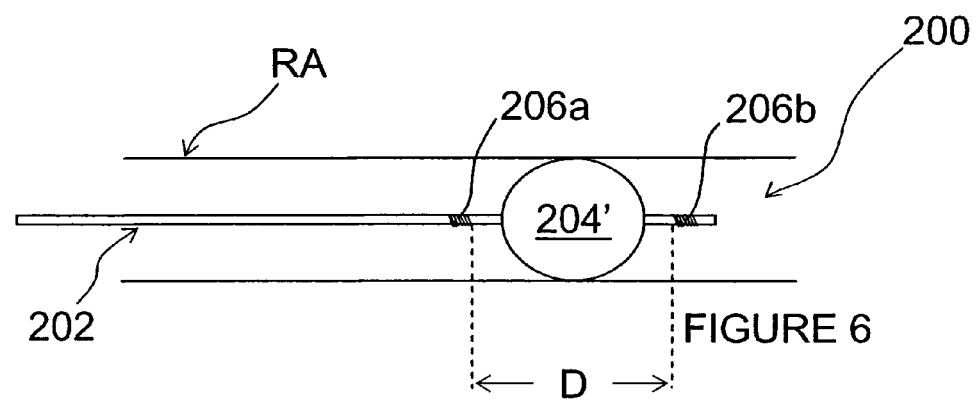
FIG. 6 is a schematic view illustrating an alternative intravascular method and apparatus of the present invention.

With reference now to FIG. 6, an alternative embodiment of apparatus 200 is described. In FIG. 5, impedance-altering element 204 illustratively comprises a semi-compliant balloon that contacts renal artery RA over a length of the artery. In FIG. 6, element 204' illustratively comprises a substantially non-compliant balloon that contacts the renal artery more focally, e.g., substantially tangentially. Balloon element 204' of FIG. 6 may have a shorter length than balloon element 204 of FIG. 5, thereby facilitating a shorter separation distance D between PEF-delivery electrodes 206.

Finite Element Analysis ("FEA") modeling of induced electric field strengths from various embodiments of intravascular PEF systems has been conducted to guide the design of preferred intravascular PEF system embodiments that reduce the required applied voltage needed to achieve a desired field strength at target tissue. Modeled variables of the intravascular PEF system designs included use (or lack thereof) of an element configured to locally increase impedance within a patient's vasculature (e.g., a balloon element), the physical design of the impedance-altering element, electrode size (not shown) and electrode spacing (not shown). Varying vessel diameter also was modeled.

Figure 8:
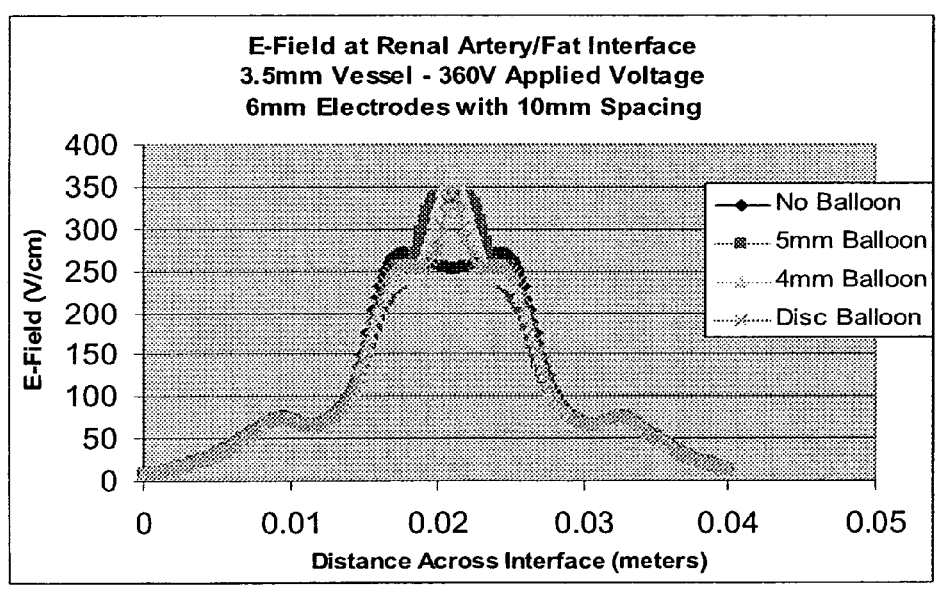
FIG. 8 is a graph illustrating modeling estimates of induced field strength along the renal artery/fat interface with the PEF systems of FIG. 7.

With reference to FIGS. 7 and 8, the FEA modeling results for four exemplary intravascular PEF systems are provided. Each of the four systems was modeled with a constant applied voltage across the electrodes (e.g., 360V), a constant electrode size (e.g., 6 mm), and a constant electrode separation distance (e.g., 10 mm) within a vessel of constant diameter (e.g., 3.5 mm). These models facilitate study of the effect of the design of the impedance-altering element on induced field strength at target tissue. In FIGS. 7 and 8, the PEF electrodes illustratively are centered with the vessel. The impedance-altering element preferably facilitates centering of the electrodes within the vessel.

Figure 4:
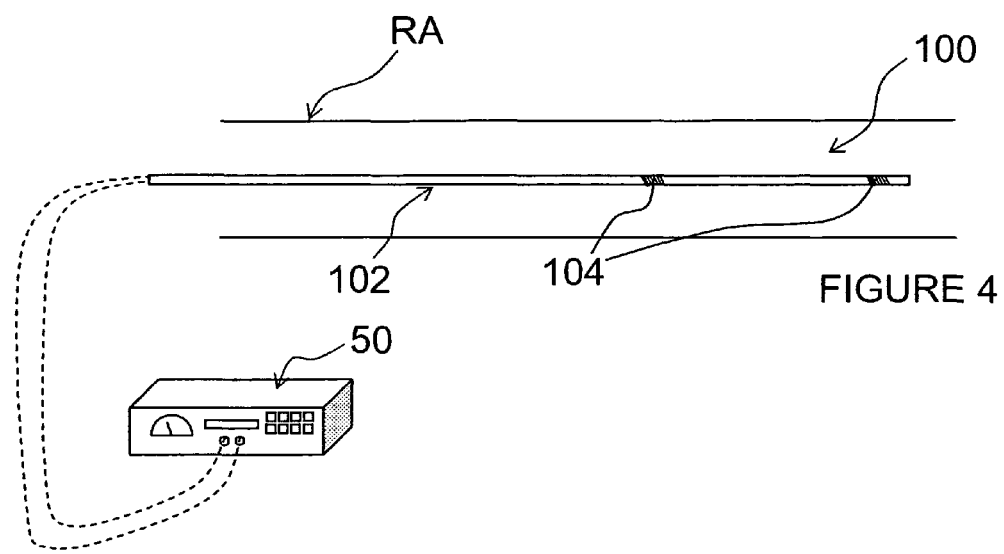
FIG. 4 is a schematic view illustrating an exemplary intravascular method and apparatus for renal neuromodulation.
Figure 7A:
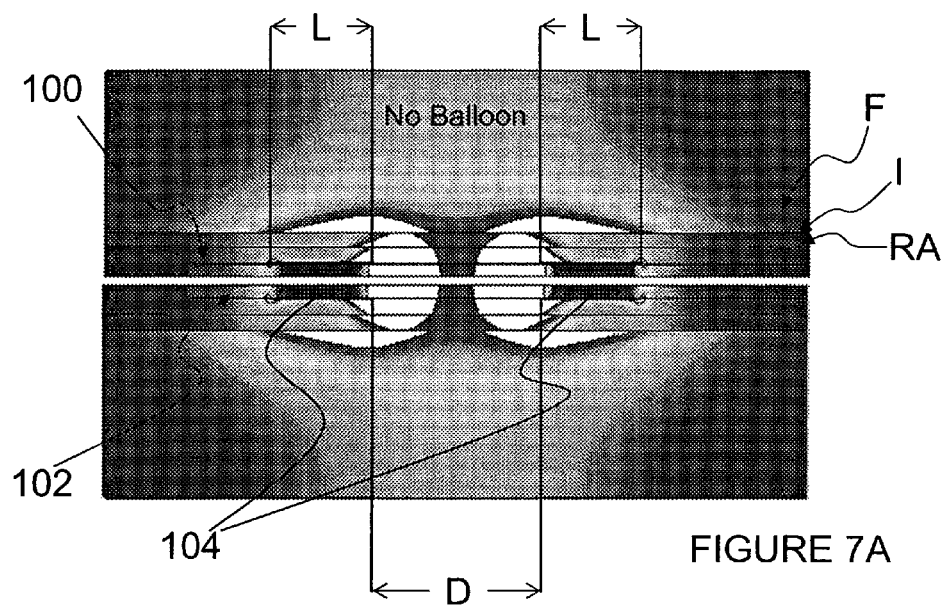
FIGS. 7A-7D are schematic cross-sectional views illustrating Finite Element Analysis modeling of spatial distributions of field strength for various intravascular PEF systems upon application of a constant magnitude applied voltage across bipolar electrodes of the PEF systems while the electrodes are positioned within a patient's renal artery.
Figure 7B:
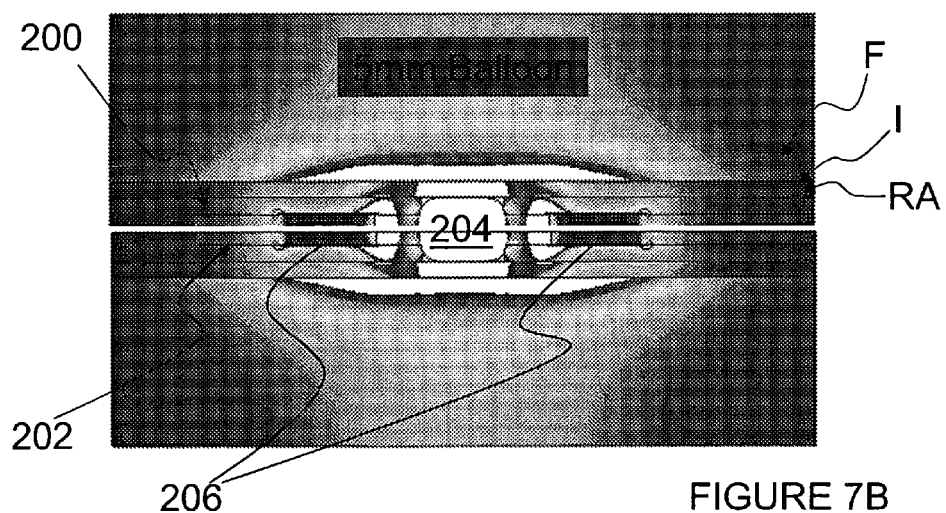
Figure 7C:
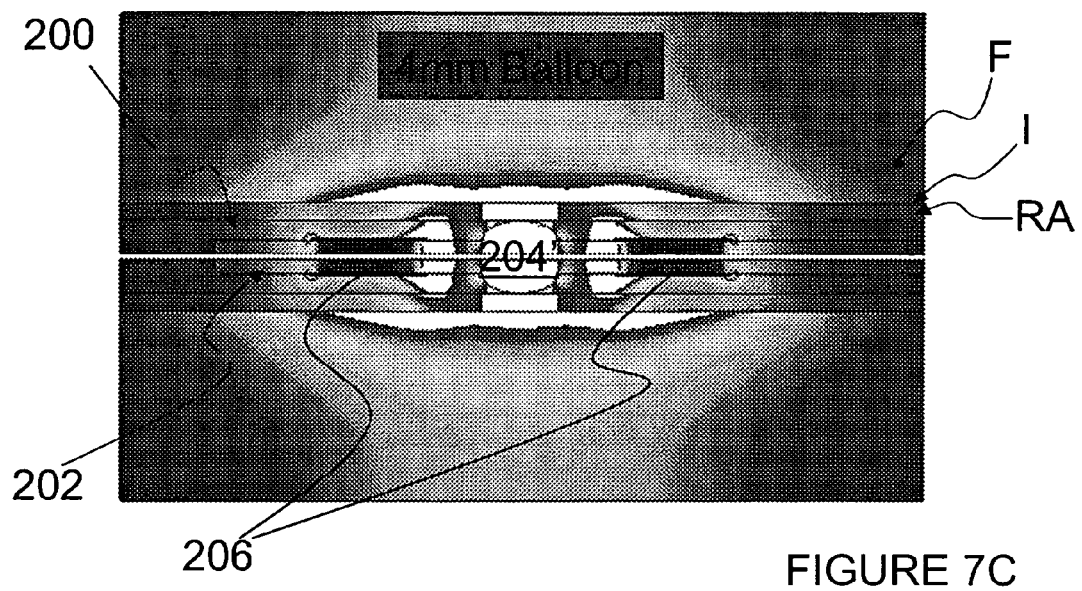
Figure 7D:
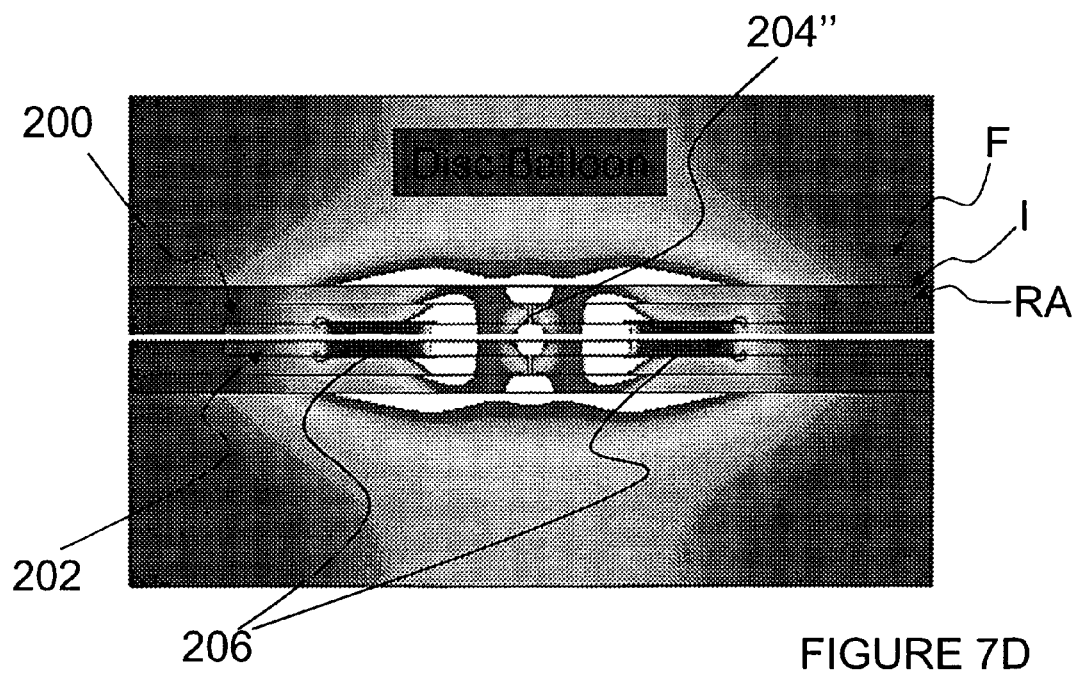

As seen in FIG. 7A, the first PEF system embodiment comprises a variation of apparatus 100 of FIG. 4 that does not comprise an impedance-altering element or that comprises an undeployed impedance-altering element, such as a deflated balloon element. As seen in FIG. 7B, the second embodiment comprises a variation of apparatus 200 of FIG. 5 comprising a 5 mm-long balloon element configured to alter impedance within a patient's vasculature, illustratively a semi-compliant balloon. In FIG. 7C, the third embodiment comprises a variation of apparatus 200 of FIG. 6 wherein balloon element 204' is 4 mm long, illustratively non-compliant, and makes only tangential contact with the wall of the renal artery RA. In FIG. 7D, the fourth embodiment comprises another variation of apparatus 200 wherein the balloon element 204" comprises a disc that occludes the renal artery RA over a very short length and makes substantially tangential wall contact.

The four embodiments each comprise a pair of bipolar PEF-delivery electrodes (electrodes 104 in FIG. 7A and electrodes 206 in FIGS. 7B-7D) with a constant separation distance D between each of the electrodes e.g., 10 mm), and a constant electrode length L (e.g., 6 mm). Similar modeling was conducted with a separation distance of 20 mm between the electrodes (not shown), and it was determined that a separation distance of less than about 20 mm is desirable in order to significantly alter the requisite magnitude of applied voltage needed with an inflated balloon to achieve a desired field strength magnitude along target neural tissue. Use of a balloon element when the electrode spacing was about 20 mm or greater showed little difference in required applied voltage between when a balloon was, and was not, used.

Electrodes 206 illustratively comprise 6 mm electrodes. Modeling also was conducted with 3 mm electrodes (not shown), and it was determined that the required applied voltage for a given field strength at target tissue generally increases as electrode length decreases. Thus, it generally is desirable to have longer electrodes, for example, electrodes preferably longer than about 1 mm, even more preferably longer than about 2 mm.

FIG. 8 provides a graph illustrating modeling estimates of induced field strength in the vicinity of target neural fibers along the renal artery RA/fat F interface I when 360V are applied across modeled bipolar electrodes of the modeled PEF system embodiments of FIG. 7. FIGS. 7 and 8 illustrate that, for the modeled PEF system designs, use of an impedance-altering element such as a balloon directs the electrical field across the wall of the renal artery. Furthermore, the peak field strength induced in the vicinity of the target neural fibers, i.e., at interface I, is increased. Thus, a lower applied voltage may be required to obtain a desired peak electric field strength at interface I when an impedance-altering element is utilized, as compared to when no impedance-altering element is provided or when the impedance-altering element is not deployed (e.g., when a balloon element is not inflated).

The modeled systems of FIGS. 7 and 8 illustrate that the contact length between the impedance-altering element and the vessel wall does not substantially alter the peak electric field strength at the interface, so long as some wall contact exists. Furthermore, shorter contact lengths, e.g., contact lengths achieved with balloon elements having lengths of less than about 5 mm, do not substantially alter the peak electric field strength. Additional FEA models (not shown) illustrate that, for the 10 mm spacing of the bipolar electrodes and a given applied voltage, use of an impedance-altering element substantially reduces changes in peak electric field strength associated with changes in vessel diameter, as compared to PEF systems without, or with undeployed, impedance-altering elements, suggesting that a substantially constant applied voltage may be used to achieve a desired electric field strength over a variety of vessel sizes when an impedance-altering element is used. This is in contrast to PEF system embodiments lacking impedance-altering elements; such embodiments might require increasing applied voltages with increasing vessel diameter in order to achieve a given desired peak electric field strength. The range of vessel sizes over which an impedance-altering PEF system may apply a substantially constant voltage to achieve a substantially similar peak field strength at the interface may, for example, vary between about 3 mm and 9 mm.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. An apparatus for intravascularly-induced neuromodulation, the apparatus comprising:
   an electric field generator; and
   an intravascular catheter comprising a shaft, an impedance-altering element, and a pair of bipolar electrodes positioned on the shaft on opposite sides of the impedance-altering element, wherein the impedance-altering element comprises an expandable, vessel occluding member;
   a first lead connected between one of the electrodes and a first terminal on the electric field generator;
   a second lead connected between the other one of the electrodes and a second terminal of opposite polarity on the electric field generator;
   at least one monitoring electrode carried by the impedance-altering element; and a current supply connected to said monitoring electrode for supplying current for monitoring a tissue property, wherein (a) the apparatus is configured for intravascular delivery of an electric field across the bipolar electrodes, and (b) the impedance-altering element is configured to locally increase impedance within a patient's vasculature between the bipolar electrodes during intravascular delivery of the electric field.

2. The apparatus of claim 1, wherein the impedance-altering element is configured to temporarily occlude blood flow within the patient's vasculature.

3. The apparatus of claim 2, wherein the impedance-altering element comprises a balloon element.

4. The apparatus of claim 3, wherein the balloon element comprises a compliant or semi-compliant balloon.

5. The apparatus of claim 3, wherein the balloon element comprises a non-compliant balloon.

6. The apparatus of claim 1, wherein the separation distance between the bipolar electrodes is not greater than about 20 mm.

7. The apparatus of claim 1, wherein each of the bipolar electrodes comprises a length of at least about 1 mm.

8. The apparatus of claim 1 wherein the at least one monitoring electrode is carried by an external surface of the impedance-altering element and is positioned to contact a vessel wall.

9. The apparatus of claim 8, wherein the monitoring electrode is configured to monitor a treatment effect in tissue exposed to the electric field.

10. The apparatus of claim 8, wherein the monitoring electrode is configured to monitor impedance of tissue proximate to the monitoring electrode.

11. The apparatus of claim 1, wherein the impedance-altering element is configured to substantially center the bipolar electrodes within the patient's vasculature.

12. The apparatus of claim 1, wherein the apparatus is configured for intravascular delivery of the electric field to neural fibers that contribute to renal function in order to modulate the neural fibers.

13. The apparatus of claim 1, wherein the impedance-altering element comprises an insulative covering positioned about a mechanical activation member.

14. The apparatus of claim 1, wherein the impedance altering element is configured to locally increase impedance within the patient's vasculature along a segment of the vasculature having a length of less than about 20 mm.

15. The apparatus of claim 1, wherein the electric field generator is configured to deliver a pulsed electric field via the electrode.

16. The apparatus of claim 15 wherein the at least one monitoring electrode is carried by an external surface of the impedance-altering element and is positioned to contact a vessel wall.

17. The apparatus of claim 16, wherein the monitoring electrode is configured to monitor electroporation induced in a target tissue by the pulsed electric field.

18. The apparatus of claim 16, wherein the monitoring electrode is configured to monitor electroporation induced in a non-target tissue by the pulsed electric field.

19. The apparatus of claim 1, wherein the electric field generator is configured to deliver energy to a target tissue via the electrode, and wherein the energy is sufficient to denervate the target tissue.

* * * * *